(12) United States Patent
Miyashita et al.

(10) Patent No.: US 7,713,328 B2
(45) Date of Patent: May 11, 2010

(54) METALLIC COLLOID PARTICLES AND PROCESS FOR PRODUCING SAME

(75) Inventors: Kiyoshi Miyashita, Tokyo (JP); Ryohei Ogawa, Tokyo (JP); Masamichi Kezuka, Tokyo (JP)

(73) Assignees: Nippon Sheet Glass Co., Ltd., Tokyo (JP); BL KK, Numazu-shi (JP)

( * ) Notice: Subject to any disclaimer, the term of this patent is extended or adjusted under 35 U.S.C. 154(b) by 113 days.

(21) Appl. No.: 11/058,363

(22) Filed: Feb. 16, 2005

(65) Prior Publication Data
US 2005/0186129 A1 Aug. 25, 2005

(30) Foreign Application Priority Data
Feb. 19, 2004 (JP) ............................. 2004-042543

(51) Int. Cl.
*B22F 1/00* (2006.01)
(52) U.S. Cl. ............................. 75/255; 424/489; 516/98
(58) Field of Classification Search ................... 75/255, 75/343, 362; 428/403, 404; 424/489; 516/98
See application file for complete search history.

(56) References Cited

U.S. PATENT DOCUMENTS 6,699,507 B1 * 3/2004 Albrecht et al. ............. 424/489
2003/0022216 A1 * 1/2003 Mao et al. ...................... 435/6

OTHER PUBLICATIONS

Schmid et al. "Ligand-Stablized Bimetallic Colloids Identified by HRTEM and EDX" (Angew. Chem. Int. Ed. Engl. 30 (1991) No. 7 874-876).*
Arnim Henglein, "Preparation and Optical Absorption Spectra of AucorePtshell and PtcoreAushell Colloidal Nanoparticles in Aqueous Solution", J. Phys. Chem. B 2000, 104, 2201-2203.*

* cited by examiner

*Primary Examiner*—George Wyszomierski
*Assistant Examiner*—Weiping Zhu
(74) *Attorney, Agent, or Firm*—Antonelli, Terry, Stout & Kraus, LLP.

(57) ABSTRACT

There are disclosed metallic colloid particles containing platinum fine particles wherein platinum colloid particles are supported on the surfaces of gold colloid particles, and the platinum fine particles have an average particle diameter of at most 5 nm; a process for producing the metallic colloid particles; a metallic corpuscular carrying body wherein the above metallic colloid particles are supported on a carrier and a process for producing the carrying body. The resultant metallic colloid particles, which have higher sensitivity, are well suited as a label for immunological measurement and protein-staining agent for various proteins.

19 Claims, No Drawings

METALLIC COLLOID PARTICLES AND PROCESS FOR PRODUCING SAME

BACKGROUND OF THE INVENTION

1. Field of the Invention

The present invention relates to a metallic colloid particles well suited as a label for immunological measurement and protein-staining agent, a process for producing the metallic colloid particles; a metallic corpuscular carrying body wherein said metallic colloid particles are supported on a carrier and a process for producing the metallic corpuscular carrying body.

2. Description of the Related Arts

An immunochromatographic assay method (hereinafter referred to as "ICA method") is known as one of procedures for immunological measurement method, and is put into practical application as a simple, easy and rapid clinical diagnosis method. According to the ICA method, it is general practice to employ an antibody which is labeled with gold colloids, since bacteria and viruses are peculiarly detected thereby. However, the ICA method using gold as a label is not said to always have sufficient sensitivity, and is required to use a label having further high sensitivity. It is taken into consideration to employ platinum colloid particles that are used for staining protein as a label for an antibody, but in the case of the ICA method, smaller particle diameter of the platinum colloid particles leads to insufficient color development.

As a countermeasure thereagainst, there are proposed metallic colloid particles wherein platinum is supported on the surfaces of gold colloid particles (refer to Japanese Patent Application Laid-Open No.262638/2003 (Heisei 15), Claim). According to this invention, there are obtainable metallic colloid particles which have sensitivity higher than that of the gold colloid particles and are well suited as a labeling agent for an immunological measurement and protein-staining agent. However depending on the type of pathogenic bacterium, infective virus concentration is extremely low, and thus there are required a labeling agent for an immunological measurement and protein-staining agent each having further high sensitivity.

SUMMARY OF THE INVENTION

An object of the present invention, which is a further improvement over the invention disclosed in the above-cited Japanese Patent Application Laid-Open No.262638/2003 (Heisei 15), is to provide metallic colloid particles having further high sensitivity and at the same time, metallic colloid particles that are well suited as a labeling agent for immunological measurements and protein-staining agent each having further high sensitivity.

Other objects thereof will become obvious from the text of the specification regarding labeling agent for immunological measurements and protein-staining agent hereinafter disclosed.

Such being the case, intensive extensive research and investigation were made by the present inventors in order to achieve the foregoing objects. As a result, it has been discovered that the objects of the invention can be achieved by metallic colloid particles containing platinum fine particles wherein platinum colloid particles are supported on the surfaces of gold colloid particles, and the supported platinum fine particles have an average particle diameter of at most 5 nm and by a process for the production of metallic colloid particles which comprises rendering both the blending amount of a reducing agent at the time of producing the gold colloid particles and the blending amount of a reducing agent at the time of reducing the platinum and supporting it on the gold colloid particles to be within a specific range. The present invention has been accomplished by such findings and information.

That is to say, the present invention provides the following.

1. Metallic colloid particles containing platinum fine particles wherein platinum colloid particles are supported on the surfaces of gold colloid particles, and the platinum fine particles have an average particle diameter of at most 5 nm;
2. The metallic colloid particles as set forth in the preceding item 1, wherein the gold colloid particles have an average particle diameter in the range of 30 to 100 nm;
3. The metallic colloid particles as set forth in the preceding item 1 or 2, wherein the molar ratio of gold to platinum is in the range of 1:1 to 1:5;
4. A process for producing metallic colloid particles which comprises reducing a gold colloid particles-formation compound in a medium to form gold colloid particles, then reducing a platinum-containing compound in the presence of the gold colloid particles so that platinum fine particles are supported on the gold colloid particles, characterized in that the platinum fine particles have an average particle diameter of at most 5 nm, and the medium is substantially free from a protective colloid formation agent;
5. The process for producing metallic colloid particles as set forth in the preceding item 4, wherein the content of the protective colloid formation agent is in the range of 0 to 200 ppm by mass expressed in terms of total carbon amount on the basis of the content of both gold and platinum;
6. The process for producing metallic colloid particles as set forth in the preceding item 5, wherein the blending amount of a reducing agent which reduces a gold colloid particles-formation compound is in the range of 1 to 3 expressed in terms of the ratio of equivalent concentration to equivalent concentration of gold, the blending amount of a reducing agent which reduces platinum-containing compound is at least 10 expressed in terms of the ratio of equivalent concentration to equivalent concentration of platinum, the platinum fine particles have an average particle diameter of at most 5 nm, and the gold colloid particles have an average particle diameter in the range of 30 to 100 nm;
7. The process for producing metallic colloid particles as set forth in the preceding item 4, wherein the gold colloid particles-formation compound is chloroauric (also termed "chlorogold" herein) acid, and the platinum-containing compound is chloroplatinic acid;
8. The process for producing metallic colloid particles as set forth in the preceding item 6, wherein sodium citrate is used as a reducing agent;
9. The process for producing metallic colloid particles as set forth in any of the preceding item 4, wherein the platinum, after being supported on the gold colloid particles, is treated with an ion exchange resin;
10. The process for producing metallic colloid particles as set forth in the preceding item 9, wherein chlorine ion concentration after the platinum is supported on the gold colloid particles is made to be at most 20 ppm by mass;
11. The process for producing metallic colloid particles as set forth in the preceding item 9, wherein sodium ion concentration after the platinum is supported on the gold colloid particles is made to be at most 20 ppm by mass;
12. Metallic colloid particles which are produced by the process as set forth in the preceding item 4;
13. A metallic corpuscular carrying body wherein the metallic colloid particles as set forth in the preceding items 1 are supported on a carrier;

14. The metallic corpuscular carrying body as set forth in the preceding item 13, wherein a material constituting the carrier is selected from the group consisting of carbon, inorganic ceramics and organic polymers;
15. A process for producing a metallic corpuscular carrying body which comprises bringing a dispersion liquid of the metallic colloid particles as set forth in the preceding item 1 into contact with a carrier;
16. The process for producing a metallic corpuscular carrying body as set forth in the preceding item 15 wherein a material constituting the carrier is selected from the group consisting of carbon, inorganic ceramics and organic polymers.

DESCRIPTION OF THE PREFERRED EMBODIMENTS

The metallic colloid particles according to the present invention are composed of gold colloid particles and platinum colloid particles that are supported on the surfaces thereof. The supported platinum fine particles are characterized by having an average particle diameter of at most 5 nm, and thereby lead to such advantages that they become metallic colloid particles having higher sensitivity than that of the prior arts, are high in absorbance, are deep in coloring and high in visual detection sensitivity in ICA method, when used as a labeling agent for immunological measurements and/or protein-staining agent.

Further, the platinum fine particles in the metallic colloid particles according to the present invention have uniform particle diameter minimized in scattering, thus forming metallic colloid particles having higher sensitivity.

The average particle diameter of gold colloid particles in the metallic colloid particles according to the present invention is not specifically limited to the extent that the working effects of the present invention are exhibited, but is preferably in the range of 30 to 100 nm. The average particle diameter thereof, when being at least 30 nm, brings about capability of sufficiently exhibiting the activity inherent in gold, thereby rendering the metallic colloid particles preferable and suitable as a labeling agent for immunological measurements and/or protein-staining agent, whereas the average particle diameter thereof, when being at most 100 nm, brings about an advantage in that platinum is more apt to be supported without stabilizing the surfaces of the gold colloid particles. In view of the foregoing, the average particle diameter thereof is preferably in the range of 40 to 80 nm.

With regard to the metallic colloid particles according to the present invention, the molar ratio of gold to platinum is not specifically limited to the extent that the average particle diameters of both gold colloid particles and platinum particles can each fall within the above-mentioned range, but is preferably in the range of 1:1 to 1:5 in terms of metal from the aspect of assuring metallic colloid particles having the average particle diameters in the above-stated range, more preferably in the range of 1:1 to 1:2 from the same aspect as the foregoing.

The average particle diameters of both gold colloid particles and platinum colloid particles are determined from the observation results by the use of a transmission electron microscope (manufactured by Topcon Co. ,Ltd. under the trade name "EM-002B", rated acceleration voltage of 200 kV).

In the following, detailed description will be given of processes for producing the metallic colloid particles according to the present invention.

In the first place, a gold colloid particles-formation compound is allowed to be contained in advance in a medium, and is reduced to form gold colloid particles. The gold colloid particles-formation compound is not specifically limited in its type provided that it is soluble in the medium, reduced by a reducing agent, and can be made into metallic colloid particles, and is exemplified by a chloride, nitrate and sulfate each of gold, and complex compound thereof. Of these, chlorogold acid is preferable from the aspect of ease of handling and the like.

The concentration of the gold colloid particles-formation compound is in the range of preferably 0.001 to 0.05% by mass, more preferably 0.003 to 0.03% by mass based on the total amount of the medium from the viewpoint of maintaining the gold colloid particles having an average particle diameter of 30 to 100 nm in a stable state.

The reducing agent which reduces the above-mentioned gold colloid particles-formation compound to form gold colloid particles is not specifically limited, but is exemplified by alcohols, citric acid/homologs, carboxylic acids, ketones, ethers, aldehydes and esters, in which two or more species may be used in combination. Examples of alcohols include methanol, ethanol, 1-propanol, 2-propanol, ethylene glycol and glycerol. Examples of citric acid/homologs include citric acid, citrate such as sodium citrate, potassium citrate and ammonium citrate. Examples of carboxylic acids include formic acid, acetic acid, fumaric acid, malic acid, succinic acid, asparagic acid and carboxylates thereof Examples of ketones include acetone and methyl ethyl ketone. Examples of ethers include diethyl ether. Examples of aldehydes include formaldehyde and acetoaldehyde. Examples of esters include methyl formate, methyl acetate and ethyl acetate. Of these, sodium citrate is preferable in particular for its high reducing power and ease of handling.

The blending amount of the reducing agent is preferably in the range of 1 to 3 expressed in terms of the ratio of equivalent concentration to equivalent concentration of gold. The above-stated ratio of equivalent concentration, when being at least 1, prevents unreacted gold ions from remaining in the liquid, whereas the ratio, when being at most 3, makes it easy to control the average particle diameter of the gold colloid particles to 30 to 100 nm, preferably 40 to 80 nm and besides makes it possible to suppress the scattering of particle diameter. The cause is considered to be due to that in the initial stage of reduction reaction by a reducing agent, the amount of generated metal nuclei is restricted to a certain extent, thus making it possible to set the number of gold atoms per gold colloid particle to a proper extent.

The ratio of equivalent concentration is determined by the valences of reduced gold and the number of electrons which can be donated per one mol of the reducing agent. For instance, in the case of using sodium citrate as the reducing agent, it functions as one-electron donor and accordingly, when the gold is of univalence, the number of moles of sodium citrate per one mole of gold is preferably in the range of 1to 3. When the gold is of trivalence, the number of moles of sodium citrate per the same is preferably in the range of 3 to 9.

As the medium which dissolves the gold colloid particles-formation compound and disperses the gold colloid particles thus formed, for instance, water, alcohols, ketones, esters and ethers are usable from the viewpoint of the production of metal colloid as mentioned hereinafter. Examples of alcohols include methanol, ethanol, 1-propanol and 2-propanol. Examples of ketones include acetone, methyl ethyl ketone and methyl isobutyl ketone. Examples of esters include methyl formate, methyl acetate and ethyl acetate. Examples of ethers include methyl ethyl ether and diethyl ether. The above-cited medium may be used alone or in combination with at least one other species, in which an aqueous medium such as water, an alcohol or a mixture thereof is preferable.

The present invention is characterized in that the medium is substantially free from a protective colloid formation agent. The protective colloid formation agent is a substance which is previously contained in a colloid liquid to maintain the dispersion stability of colloid particles, and which sticks to the surfaces of the colloid particles to form a protective colloid. Examples of the protective colloid formation agent include, for instance, water-soluble high molecular substances such as polyvinyl alcohol, polyvinyl pyrrolidone and gelatin, surfactants, high molecular chelating agent {for instance, such compounds as described on Japanese Patent Application Laid-Open No. 279818/2000 (Heisei 12) paragraph 0013}.

In the case of using a protective colloid formation agent, removal of the agent is usually made necessary through heating, reduction or the like for the sake of activity development, thereby sometimes exerting evil influence on metallic colloid particles such as aggregation of metallic colloid due to the above-mentioned procedure. As opposed to the foregoing, the present invention dispenses with such procedure because of nonuse of protective colloid formation agent, and thereby precludes adverse influence upon the metallic colloid particles.

After the gold colloid particles have been formed by the above-mentioned method, a platinum-containing compound is added to a dispersion liquid of the gold colloid, or the gold colloid particles thus formed are added to a liquid in which a platinum-containing compound is dissolved in a medium. The platinum-containing compound is not specifically limited in its type provided that it is soluble in the medium, reduced by a reducing agent, and can be made into metallic colloid particles, and is exemplified by a chloride, nitrate and sulfate each of platinum, and complex compound thereof. Of these, chloroplatinic acid is preferable from the viewpoint of contriving the uniformization of colloid particles diameter.

The concentration of the platinum-containing compound is regulated to the range of preferably 1 to 5 moles, more preferably 1 to 2 moles of platinum atoms based on one mole of gold atom.

Next, the platinum-containing compound is reduced, and the platinum is supported on the surfaces of gold colloid. Examples of reducing agent to be used include the reducing agent same as or similar to that used for forming gold colloid particles. The reducing agent for forming gold colloid particles and the reducing agent for supporting platinum may be the same as or different from each other, but from the standpoint of workability, use of the same reducing agent is preferable. In the present invention, use of sodium citrate is most preferable as mentioned above.

The blending amount of the reducing agent in the case of reducing and supporting platinum on gold colloid particles is preferably at least 10 expressed in terms of the ratio of equivalent concentration to equivalent concentration of platinum. By increasing the blending amount of the reducing agent, it is made possible to generate much metal nuclei and control the particle diameter of each platinum particle in the initial stage of platinum reduction reaction. The ratio of equivalent concentration, when being at least 10, facilitates the suppression of average particle diameter of platinum particles of to at most 5 nm and besides, enables to restrain the scattering of platinum particles diameter.

The gold colloid particles which have already formed colloid particles are stably present in the medium and accordingly, the average particle diameter thereof is not changed by further adding the reducing agent.

In the present invention, a platinum-containing compound is added to a dispersion liquid of the gold colloids, or the gold colloid particles thus formed are added to a liquid in which a platinum-containing compound is dissolved in a medium. Thereafter the platinum-containing compound is reduced, and platinum is supported on the gold colloid particles. It is thought that under ordinary conditions, the platinum-containing compound is reduced, whereby platinum colloid particles are formed and supported on the gold colloid particles. It is important in the present invention to control the platinum colloid particles diameter so that the particles diameter of platinum fine particles that are supported on the gold is made to be at most 5 nm.

Usually in order to maintain platinum colloids having somewhat concentration and fine particle diameter in a dispersion medium, a protective colloid is indispensable, and a protective colloid formation agent is required to be contained in the dispersion medium.

As opposed to the foregoing, the process for producing the metallic colloids according to the present invention is characterized by being substantially free from a protective colloid formation agent as described hereinbefore. Thus colloid particles having a particle diameter of at most 5 nm are maintained in a dispersion state without incorporating a protective colloid formation agent, by controlling platinum ion concentration, content of the reducing agent and reaction time.

The platinum colloid particles according to the present invention have favorable dispersion stability, thereby enabling to maintain stable dispersibility for a practically sufficiently long period of time, for instance, 3 to 30 days even if being substantially free from a protective colloid formation agent, which means that the content of the agent in the medium is in the range of 0 to 200 ppm by mass, approximately expressed in terms of total carbon on the basis of the content of gold and platinum.

In the following, specific description will be given of a method for producing the platinum colloid particles having favorable dispersion stability using water as a dispersion medium, even if being substantially free from a protective colloid formation agent.

There is used as water, pure water such as distilled water, ion exchanged water, ultrafiltered water or the like, which is sufficiently boiled to remove dissolved oxygen. To the metallic salt aqueous solution which has been prepared using the pure water as mentioned above, is added an aqueous solution of a reducing agent so that the concentration of the metallic salt becomes $1 \times 10^{-4}$ to $15 \times 10^{-4}$ mole/liter, approximately and the amount of the reducing agent becomes about 1 to 20 times equivalent based on the metallic salt. Subsequently reaction is advanced in a boiling state for about 30 to 300 minutes and thereafter stopped by rapidly cooling to room temperature.

The platinum colloid particles having favorable dispersion stability can be produced in such a manner, even if the medium is substantially free from a protective colloid formation agent.

Since the medium is substantially free from a protective colloid formation agent as mentioned above in the present invention, it is made possible to dispense with a treatment of removing the colloid formation agent from the gold colloid particles on which the platinum colloid particles are supported, for instance, heating or reduction, whereby the production process can be simplified. Moreover, the process is advantageous in being no need of taking into consideration the aggregation of platinum colloid particles due to a step of removing the colloid formation agent, generation of residue and impurity and the like.

Under ordinary production conditions, there are obtainable metallic colloid particles wherein platinum fine particles having an average particle diameter of at most 5 nm are supported on the surfaces of the gold colloid particles having an average particle diameter of 30 to 300 nm. An embodiment in which the surfaces of the gold colloid particles are covered with platinum in part or in whole is included in the scope of the present invention without precluding an embodiment in which the surfaces of the gold colloid particles are covered with platinum in the form of thin film.

It is possible by the above-mentioned method to further highly concentrate the metallic colloid particles in the liquid in which metallic colloid particles to be produced are dispersed. The preparation method comprises heat treating the colloid liquid under a mild condition, for instance, non-boiling so that dispersion medium in the colloid liquid is distilled away, and the liquid is concentrated. In the case where a boiling state takes place, for instance, depending upon the conditions of concentration, the colloid particles are liable to be aggregated by the influence of convection and/or break of bubbles. Accordingly, a mild condition is preferably selected so as not to give rise to the aggregation of the colloid particles. In the case of the dispersion medium being water, it is possible to control the concentration of the colloid solution by distilling away the water under atmospheric or reduced pressure at a temperature of 50° C. to 90° C., approximately over a period of 15 to 240 minute, while altering degree of vacuum, temperature and concentration time.

In the process for producing the metallic colloid particles according to the present invention, it is preferable when desired to remove unreacted metallic salts and the reducing agent by passing the reaction liquid after reaction completion through a column packed inside with an ion exchange resin. It is preferable to control concentrations of both chlorine ions and sodium ions to at most 20 ppm by mass by a treatment with the ion exchange resin. By the above-mentioned control to at most 20 ppm by mass, it is possible to preclude a factor of inhibiting the activity of the metallic colloid particles according to the present invention.

It is also possible to use the metallic colloid particles according to the present invention as a metallic corpuscular carrying body by supporting on a carrier. The carrier to be used is not specifically limited provided that it can maintain the metallic colloid particles in a highly dispersed state, but is exemplified by a variety of materials. The materials constituting the carrier are exemplified by carbon materials, inorganic ceramics and organic polymers. Suitable carrier is composed of any of the materials having a surface area to some extent. Examples of the carbon materials include activated carbon, charcoal, carbon black, graphite, carbon fiber, carbonaceous hollow fiber, carbon nanotube and carbon nanophone. Examples of the inorganic ceramics include alumina, titania, magnesia, silica, silica-alumina, zirconia, zeolite, silicon carbide, silicon nitride, glass and clay minerals. Examples of organic polymers include polyester based resin such as polyethylene terephthalate, polybutylene terephthalate, polyethylene naphthalate and polycarbonate; acrylic resin such as polymethyl methacrylate; olefinic resin such as polyethylene, polypropylene, plymethylpentene and polymers containing alicyclic structure; celluloses such as cellophane, diacetyl cellulose, triacetyl cellulose and acetyl cellulose butylate; polyvinyl chloride, polyvinylidene chloride, polyvinyl alcohol, ethylene-vinyl aceate copolymer, polystyrene; polysulfone, polyether ether ketone, polyether sulfone, polyether imide, polyimide, fluororesins and plyamide.

In the case of using the metallic colloid particles by supporting on a carrier, the metallic colloid particles are contained in an amount of preferably 0.1 to 3 parts by mass, approximately based on 100 parts by mass of the carrier components. The amount of the metallic colloid particles, when being at least 0.1 part by mass, enables to sufficiently exhibit the working effect on dyeing reaction, color development reaction and the like, whereas the amount, when being at most 3 parts by mass, brings about a highly uniformly dispersed state of the metallic colloid particles on the carrier.

The configuration and shape of the carrier is not specifically limited, but is exemplified by rod, fiber, woven fabric, nonwoven fabric, film, sheet, platy body and powder. Of these, is preferable the carrier composed of glass fiber or flaky glass, the surface of which is easily made porous when being subjected to a chemical treatment by the use of acid/alkali solution. Since the pores of the porous body usually have an average particle diameter of about 1 to 10 nm, the above-described colloid particles are capable of successfully penetrating in the pores of the porous body and of being firmly fixed thereto.

The present invention also provides the carrier, and metallic carrying body having metallic nanocolloid particles which originate from the above-mentioned material for supporting and which are supported on the carrier. The substrate in this metallic carrying body is exemplified by the substrate same as that cited in the process for producing the metallic carrying body.

As a method for supporting the metallic colloid particles according to the present invention on the carrier, there are usable well known methods as supporting methods that are usually used for preparing a catalyst and the like. For instance, there are usable a method which comprises dispersing the metallic colloid particles obtained by the above-stated method in a dispersion medium, and immersing the carrier in the resultant dispersion liquid; and a pore filling method using an aqueous dispersion medium which comprises bringing a dispersion liquid corresponding to water absorbing capacity of a carrier that has been measured in advance into contact with the carrier so as to support the metallic colloid particles on the pores and surfaces of the carrier.

It is also possible to immerse a carrier in a medium during the production course of the metallic colloid particles as mentioned above to support the same on the carrier.

In summarizing the working effects and industrial utilizability of the present invention, the platinum fine particles supported on the gold colloid particles have an average particle diameter of at most 5 nm along with minimized scattering of particle diameter and high uniformity thereof, and hence there are obtainable the metallic colloid particles which have sensitivity higher than that of the prior arts and can be made to be labels for antigen and antibodies by a conventional method, and are usable for ICA method and other immunological measurement method. In addition, the metallic colloid particles, which adsorb and accumulate onto proteins, assuming black color as is the case with ordinary platinum colloid particles, can be used as a staining agent for various proteins. Further, platinum fine particles present on the surface of the metallic colloid particles are imparted with high oxidation/reduction catalytic activity, and thereby enable proteins to be detected with high sensitivity, when used in combination with a color developing agent which assume a color by oxidation/reduction reaction. The color developing agent is exemplified, for instance, by 3, 3', 5, 5'-tetramethylbenzidine.

In what follows, the present invention will be described in more detail with reference to a working example, which shall never limit the present invention thereto.

{Evaluation method} Evaluation of color development properties by the use of 3, 3', 5, 5'-tetramethylbenzidine (TMB).

Color development properties were evaluated by the use of TMB from the difference in the extent of change to blue color due to peroxidase reaction according to the following specific procedures.
1) Samples were prepared by diluting the metallic colloid solution that was prepared by the methods in the example and comparative example so that the absorbance at 560 nm was made to be at most 0.010.
2) The samples (200 μL of metallic colloid solution) were each incorporated with 200 μL of TMB, and cultured at 30° C. for 5 minutes.
3) 2N sulfuric acid of 200 μL as the reaction terminator was added to each sample, thereafter absorbance at a wavelength of 450 nm was measured with a spectrophotometer, and evaluations were made by the difference in absorbance (ΔO.D.) before and after the TMB reaction. The sensitivity increases with an increase in ΔO.D. Accordingly, a metallic colloid solution having high sensitivity is excellent as labeling agent for immunological measurements and protein-staining agent. The absorbance was defined in accordance with Lambert-Beer's law, wherein A in A=eCl was defined as the absorbance {e; molar absorptibity ($M^{-1}$ $cm^{-1}$)},
C; molar concentration (M), l; optical path length

EXAMPLE 1

Instruments including a 1500 milliliter (mL) flask, two 100 mL Erlenmeyer flasks, two 200 mL Erlenmeyer flasks, a reflux condenser and a stirrer were immersed in aqua regia overnight, and were sufficiently washed with ion exchanged and ultrafiltered pure water. The 1500 mL flask was charged with 850 mL of the ion exchanged and ultrafiltered pure water and the stirrer, while the reflux condenser was installed above the flask, and was heated to raise the temperature up to 100° C. In order to remove dissolved oxygen in the pure water, boiling was continued as such for further one hour.

On the other hand, chlorogold acid (H Au $Cl_4$.$4H_2O$) in an amount of 52 mg (25 mg expressed in terms of gold) was weighed and placed in the 100 mL Erlenmeyer flask A, where ion exchanged and ultrafiltered pure water was added to attain a total volume of 25 mL. Further 0.05 g of sodium citrate was weighed and placed in the 200 mL Erlenmeyer flask B, where ion exchanged and ultrafiltered pure water was added to attain a total volume of 10 mL. Dissolved oxygen in the pure water was removed and thereafter, aqueous solution of chloroauric acid was added to the 1500 mL flask from the 100 mL Erlenmeyer flask A, and the content of the 1500 mL flask was heated to raise the temperature up to 100° C. and was boiled for 30 minutes to remove dissolved oxygen in the pure water. Subsequently, the aqueous solution of sodium citrate was gradually added thereto from the 200 mL Erlenmeyer flask B so as to maintain the boiling state. The reason for maintaining the boiling state was to maintain the concentration of dissolved oxygen as low as possible, while vaporized water was returned to the 1500 mL flask by refluxing operation.

The reaction solution had a gold concentration of 25 mg/L=$1.27\times10^{-4}$ mol/L=$3.81\times10$–4 N, and the ratio of sodium citrate molar concentration to gold molar concentration of about 1.48, wherein sodium citrate molar concentration is molar concentration at the time when aqueous solution of sodium citrate was prepared.

Next, chloroplatinic acid ($H_2PtCl_6$.$6H_2O$) in an amount of 133 mg (50 mg expressed in terms of platinum) was weighed and placed in another 100 mL Erlenmeyer flask C, where ion exchanged and ultrafiltered pure water was added to attain a total volume of 25 mL. Further 1.0 g of sodium citrate was weighed and placed in another 200 mL Erlenmeyer flask D, where ion exchanged and ultrafiltered pure water was added to attain a total volume of 100 mL.

After the lapse of about 30 minutes from the charge of aqueous solution of chloroauric acid, an aqueous solution of chloroplatinic acid was placed in the 1500 mL Erlenmeyer flask from the 100 mL Erlenmeyer flask C, and the content of the 1500 mL flask was heated to raise the temperature up to 100° C. Subsequently, the aqueous solution of sodium citrate was gradually added thereto from the 200 mL Erlenmeyer flask D so as to maintain the boiling state. The reason for maintaining the boiling state and the procedure of returning vaporized water are each the same as the foregoing.

The reaction solution had a platinum concentration of 50 mg/L=$2.56\times10^{-4}$ mol/L=$1.02\times10^{-3}$ N, and the ratio of sodium citrate molar concentration to platinum molar concentration of about 13.28. The sodium citrate molar concentration is molar concentration at the time when aqueous solution of sodium citrate was prepared.

The aqueous solution of sodium citrate was wholly added to the 1500 mL flask from the 200 mL Erlenmeyer flask D, and thereafter, the reducing reaction was continued under a boiling state, and was stopped after 120 minutes from the start of the reaction, whereupon the reaction liquid was rapidly cooled to room temperature. The reaction liquid thus cooled was passed through a column packed inside with an ion exchange resin Umberlite MB-1 (trade name, manufactured by Japan Organo Co., Ltd.), so that metallic ions and the reducing agent remaining in the reaction liquid were removed to obtain stable metallic colloid liquid. Thus measurements were made of the metallic colloid particles concentration in the metallic colloid liquid by means of plasma emission spectrochemical analysis and of average particle diameter thereof by the use of a transmission electron microscope. As a result, the gold colloid particles had a concentration of 20 mg/L and an average particle diameter of 50 nm, and the platinum fine particles supported thereon had a concentration of 40 mg/L and an average particle diameter of 3 nm.

Chlorine ion concentration, sodium ion concentration and citric acid content before the treatment with the ion exchange resin were 60 mg/L, 250 mg/L and 580 mg/L, respectively, and were at most 1 mg/L, 4 mg/L and at most 1 mg/L, respectively after the treatment with the ion exchange resin.

As a result of evaluation of the metallic colloid particles that were prepared in the above-described manner by the foregoing evaluation method, ΔO. D. was 1.048 showing high sensitivity.

COMPARATIVE EXAMPLE 1

The procedure in Example 1 was repeated to obtain metallic colloid particles except that 1.0 g of sodium citrate was weighed and placed in the 200 ml Erlenmeyer flask B. Gold concentration, platinum concentration and molar concentration ratios of sodium citrate to gold concentration and platinum concentration each in reaction solutions were as follows.
gold concentration; 25 mg/L=$1.27\times10^{-4}$ mol/L=$3.81\times10^{-4}$ N
molar concentration ratio of sodium citrate to gold concentration; about 29.6 (the sodium citrate molar concentration is molar concentration at the time when aqueous solution of sodium citrate was prepared).

platinum concentration; 50 mg/L=$2.56 \times 10^{-4}$ mol/L=$1.02 \times 10^{-3}$ N molar concentration ratio of sodium citrate to platinum concentration; about 13.28

(the sodium citrate molar concentration is molar concentration at the time when aqueous solution of sodium citrate was prepared).

The gold colloid particles had a concentration of 20 mg/L and an average particle diameter of 15 nm, and the platinum fine particles supported thereon had a concentration of 40 mg/L and an average particle diameter of 7 nm.

Chlorine ion concentration, sodium ion concentration and citric acid content before the treatment with the ion exchange resin were 60 mg/L, 250 mg/L and 580 mg/L, respectively, and were at most 1 mg/L, 4 mg/L and at most 1 mg/L, respectively after the treatment with the ion exchange resin.

As a result of evaluation of the metallic colloid particles that were prepared in the above-described manner by the foregoing evaluation method, ΔO. D. was 0.688.

It is understandable therefrom that the metallic colloid particles in Example 1 had a ΔO. D value about 1.52 times as high as a ΔO. D. value of Comparative Example 1, thereby showing high sensitivity. This is considered to be attributable to the difference between the particle diameters of gold colloid particles/platinum colloid particles in the metallic colloid of Example 1 and the particle diameters of gold colloid particles/platinum colloid particles in the metallic colloid of Comparative Example 1.

What is claimed is:

1. A labeling agent for an immunochromatographic assay method, comprising metallic colloid particles containing platinum fine particles wherein platinum colloid particles are supported on the surfaces of gold colloid particles, wherein the platinum fine particles have an average particle diameter of at most 5 nm, and wherein the gold colloid particles have an average particle diameter in the range of 30 to 100 nm, the metallic colloid particles having a property that they can be used in the immunochromatographic assay method.

2. The labeling agent for an immunochromatographic assay method according to claim 1, wherein the molar ratio of gold to platinum is in the range of 1:1 to 1:5.

3. The labeling agent for an immunochromatographic assay method according to claim 1, which is substantially free from a protective colloid formation agent.

4. The labeling agent for an immunochromatographic assay method according to claim 3, wherein the gold colloid particles have been formed in a medium substantially free from a protective colloid formation agent.

5. The labeling agent for an immunochromatographic assay method according to claim 1, wherein the average particle diameter of the gold colloid particles is in the range of 40 to 80 nm.

6. The labeling agent for an immunochromatographic assay method according to claim 1, wherein the molar ratio of gold to platinum is in the range of 1:1 to 1:2.

7. The labeling agent for an immunochromatographic assay method according to claim 1, wherein the gold colloid particles have been formed in a medium substantially free from a protective colloid formation agent.

8. The labeling agent for an immunochromatographic assay method according to claim 1, further comprising a color developing agent which assumes a color by oxidation/reduction reaction.

9. In an immunochromatographic assay method, the improvement comprising employing an antibody which is labeled with the labeling agent according to claim 1.

10. A labeling agent for an immunochromatographic assay method, comprising metallic colloid particles produced by a process which comprises reducing a gold colloid particles-formation compound in a medium to form gold colloid particles, then reducing a platinum-containing compound in the presence of the gold colloid particles so that platinum fine particles are supported on the gold colloid particles, and wherein the platinum fine particles have an average particle diameter of at most 5 nm, the gold colloid particles have an average particle diameter in the range of 30 to 100 nm, and the medium is substantially free from a protective colloid formation agent, the metallic colloid particles having a property that they can be used in the immunochromatographic assay method.

11. The labeling agent for an immunochromatographic assay method according to claim 10, wherein the content of the protective colloid formation agent is in the range of 0 to 200 ppm by mass expressed in terms of total carbon amount on the basis of the content of both gold and platinum.

12. The labeling agent for an immunochromatographic assay method according to claim 11, wherein the blending amount of a reducing agent which reduces gold colloid particles-formation compound is in the range of 1 to 3 expressed in terms of the ratio of equivalent concentration to equivalent concentration of gold, and the blending amount of a reducing agent which reduces platinum-containing compound is at least 10 expressed in terms of the ratio of equivalent concentration to equivalent concentration of platinum.

13. The labeling agent for an immunochromatographic assay method according to claim 10, wherein the gold colloid particles-formation compound is chloroauric acid, and the platinum-containing compound is chloroplatinic acid.

14. The labeling agent for an immunochromatographic assay method according to claim 12, wherein sodium citrate is used as a reducing agent.

15. The labeling agent for an immunochromatographic assay method according to claim 10, wherein the platinum, after being supported on the gold colloid particles, has been treated with an ion exchange resin.

16. The labeling agent for an immunochromatographic assay method according to claim 15, wherein chlorine ion concentration after the platinum has been supported on the gold colloid particles is made to be at most 20 ppm by mass.

17. The labeling agent for an immunochromatographic assay method according to claim 15, wherein sodium ion concentration after the platinum has been supported on the gold colloid particles is made to be at most 20 ppm by mass.

18. The labeling agent for an immunochromatographic assay method according to claim 10, further comprising a color developing agent which assumes a color by oxidation/reduction reaction.

19. The labeling agent for an immunochromatographic assay method according to claim 10, wherein the average particle diameter of the gold colloid particles is in the range of 40 to 80 nm.

* * * * *